(12) United States Patent
Leon et al.

(10) Patent No.: US 6,353,096 B1
(45) Date of Patent: Mar. 5, 2002

(54) PROCESS OF USE IN CONVERTING THE 4" (S)-OH FUNCTIONAL GROUP OF THE CLADINOSE UNIT OF AN AZAMACROLIDE TO 4"(R)-NH2

(75) Inventors: Patrick Leon, Tassin la Demi Lune; Frederic Lhermitte, Saint Symphorien d'Ozon; Ronan Guevel, Lyons; Denis Pauze, Solaize; Laurent Garel; Gilles Oddon, both of Lyons, all of (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/484,648

(22) Filed: Jan. 18, 2000

Related U.S. Application Data

(60) Provisional application No. 60/127,400, filed on Apr. 1, 1999.

(51) Int. Cl.[7] .......................... C07H 1/00; C07H 17/08
(52) U.S. Cl. ..................................... 536/7.4; 536/18.5
(58) Field of Search ..................... 536/7.2, 7.4, 18.5

(56) References Cited

FOREIGN PATENT DOCUMENTS

| EP | 0 508 699 | 10/1992 |
|----|-----------|---------|
| EP | 0 549 040 | 6/1993 |
| WO | WO 99 12542 | 3/1999 |

OTHER PUBLICATIONS

K. Shankaran et al.; "Preparation and Activities of 4"–Epi and 4"–deoxy–4"–Amino Analogs Derived from 9–Deoxo–8a–Aza–8a–Homoerythromycin A.", Bioorganic and Medicinal Chemistry Letters, vol. 4, No. 9, 1994, pp. 1111–1116, XP002118137.

*Primary Examiner*—Elli Peselev
(74) *Attorney, Agent, or Firm*—Frommer Lawrence & Haug LLP; William S. Frommer; Thomas J. Kowalski

(57) ABSTRACT

The subject-matter of the invention is a process for the stereoselective preparation of a compound of general formula I

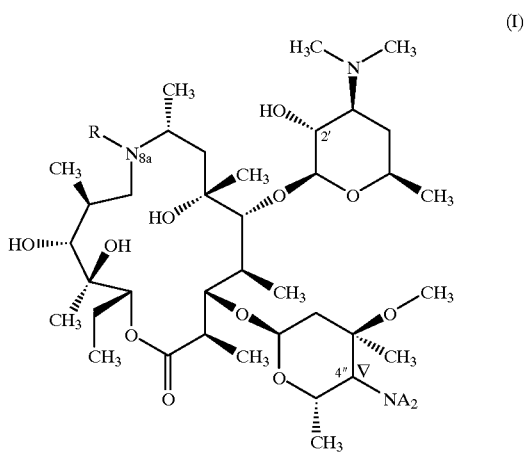

by stereoselective displacement by a nitrogenous nucleophilic compound of the activated alcohol functional group present at this 4" position in a corresponding derivative of formula II.

32 Claims, No Drawings

PROCESS OF USE IN CONVERTING THE 4" (S)-OH FUNCTIONAL GROUP OF THE CLADINOSE UNIT OF AN AZAMACROLIDE TO 4"(R)-NH2

RELATED APPLICATIONS

This application claims priority from U.S. application Ser. No. 60/127,400, filed, Apr. 1, 1999 and from French Application 99 00459, filed Jan. 18, 1999. Reference is also made to U.S. Provisional patent application Ser. No. 60/128,383, filed, Apr. 8, 1999 and French application 99 03885, filed Mar. 29, 1999. Each of these applications, and each document cited or referenced in each of these applications is hereby incorporated herein by reference. It is hereby stated that the inventive entity of each of U.S. Provisional patent application Ser. No. 60/128,383, filed, Apr. 8, 1999, French application 99 03885, filed Mar. 29, 1999 and any full U.S. utility application claiming priority from either or both of U.S. Provisional patent application Ser. No. 60/128,383, filed, Apr. 8, 1999 and French application 99 03885, filed Mar. 29, 1999 is not "another" or "others" as to the inventive entity of this application, and vice versa. In addition, each document cited herein ("herein cited documents") and each document referenced or cited in herein cited documents are hereby incorporated by reference.

The subject-matter of the present invention is a process of use in converting the 4" (S)-OH functional group of the cladinose unit of an azamacrolide to 4" (R)—NH2.

The present invention relates more particularly to the field of macrolide antibiotics of erythromycin type and more particularly their azamacrolide derivatives which form the subject-matter of Patent EP 508,699 and which correspond to the following general formula:

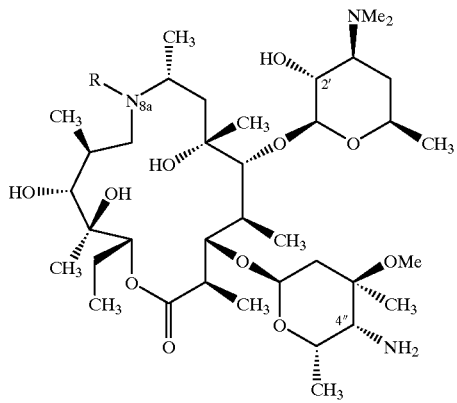

in which R is a hydrogen atom or a $C_1$–$C_{10}$ alkyl, $C_2$–$C_{10}$ alkenyl or $C_6$–$C_{12}$ arylsulphonyl group, which are, if appropriate, substituted.

These compounds are obtained from erythromycin and their synthesis involves two major stages:
 the creation of the 8a-azalide macrocycle starting from the (Z) oxime, which is subjected to a stereospecific Beckmann rearrangement, and
 the modification of the cladinose group at the 4" position, which consists of the conversion of the 4" (S)-OH to 4" (R)-$NH_2$, that is to say with inversion of configuration, which can be illustrated as follows:

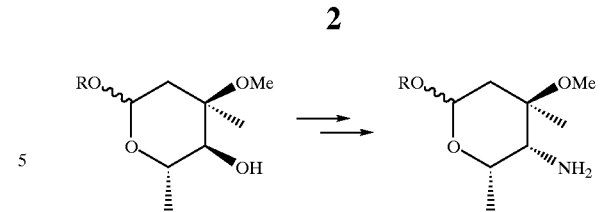

In fact, the route currently used to provide for this conversion of the 4" (S)-OH to 4" (R)-$NH_2$ is not completely suitable for production on an industrial scale.

It involves, successively, an oxidation of the hydroxyl functional group at the 4" position to a ketone functional group and then the conversion of this ketone to an oxime, which, by reduction, results in an approximately 1 to 1 mixture of the expected amino derivative and of its 4" epimer.

This synthetic route consequently has the major disadvantage of requiring the formation of $sp^2$ C-4" intermediates and thus of losing the stereochemical information initially present at the $sp^3$ C-4" of the cladinose unit. This result is all the more of a nuisance since the isomers, acquired on conclusion of this synthetic route, are obtained with a low yield of about 20% and are in addition difficult to separate. Thus, for a crude reaction yield of about 20%, only approximately 7% of the amino derivative with inversion of configuration is obtained.

The object of the present invention is specifically to provide a new access route to these derivatives, aminated at the 4" position, which advantageously makes it possible to retain a significant stereoselectivity and provides a satisfactory yield.

More specifically, a first subject-matter of hi the present invention is a process for the preparation of a compound of general formula I

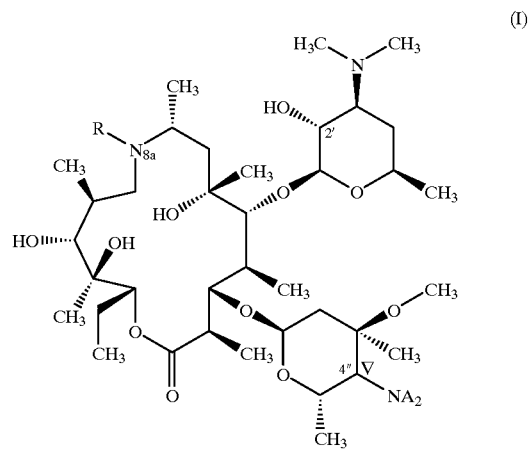

in which:
 R is a hydrogen atom or a $C_1$–$C_{10}$ alkyl, $C_2$–$C_{10}$. alkenyl or $C_6$–$C_{12}$ arylsulphonyl group, which are, if appropriate, substituted, and
 A, which are identical or different, are
  a hydrogen atom,
  a nitrogen atom, if appropriate substituted,
  a $C_1$–$C_4$ alkyl group, which is optionally substituted by one or more aryl groups, which are, if appropriate, substituted, an $R_2CO$ or $R_2SO_2$ group, with $R_2$ being a hydrogen atom, a $C_1$–$C_{18}$ alkyl group or an aryl group, which are, if appropriate, substituted, ▽ means that the C in the 4" position has undergone an inversion of configuration with respect to the formula II, from a compound of general formula II

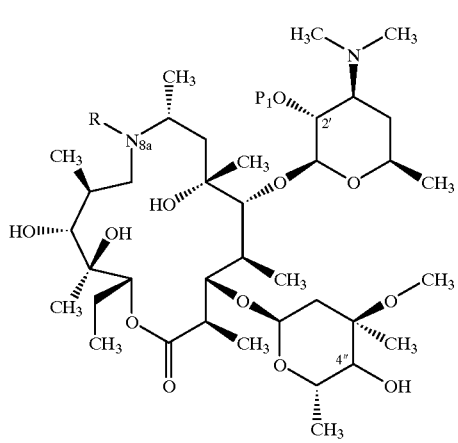

(II)

with:

R as defined in general formula I and $P_1$ being a protective group for the hydroxyl functional group at the 2' position, characterized in that it comprises at least the stages consisting in:

activating the hydroxyl functional group at the 4" position in the compound of general formula II, in order to obtain a compound of general formula III

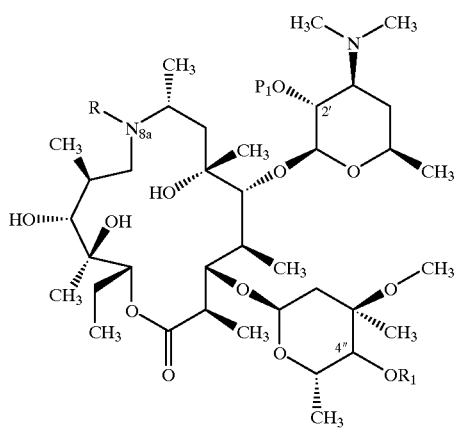

(III)

in which:

R and $P_1$ are as defined in general formulae I and II and $OR_1$ is a leaving group, bringing the said compound of general formula III thus obtained into contact with a nitrogenous nucleophilic derivative under conditions which are sufficient to allow the stereoselective displacement of the hydroxyl functional group activated by the said nitrogenous nucleophile, and deprotecting the hydroxyl functional group at the 2' position, in order to result in the expected compound of general formula I.

The claimed process thus has the significant advantage of not requiring the formation of the $sp^2$ C-4" intermediate necessarily generated in the prior synthetic route discussed above. It involves only an inversion of configuration at the 4" position and this inversion is obtained efficiently by displacement by a nitrogenous nucleophile of the activated alcohol functional group present at this 4" position.

Consequently, the claimed process proves to be particularly advantageous for preparing with a very satisfactory yield, a 4" (R)-$NA_2$ derivative of general formula I'

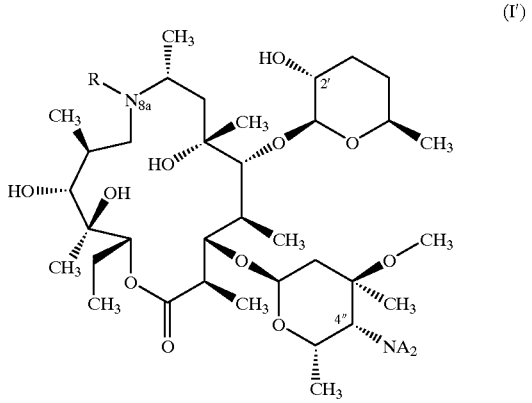

(I')

with A and R as defined above from a 4" (S)-OH azamacrolide derivative of general formula II'

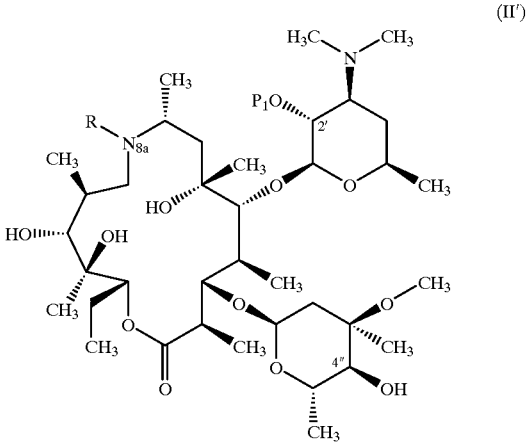

(II')

with R and $P_1$ as defined above.

As regards the leaving group represented by $OR_1$ in general formula III, it is preferably selected from $C_1$–$C_{20}$ alkyl sulphonates, $C_5$–$C_6$ aryl or heteroaryl sulphonates or $C_6$ to $C_{26}$ alkylaryl sulphonates, which are substituted, if appropriate, by one or more halogen atoms, preferably fluorine, and/or a nitro, cyano or trifluoromethyl group.

The leaving group represented by $OR_1$ in general formula III is preferably a group selected from mesylate, triflate and tosylate and is more preferably a triflate group.

Use may in particular be made according to the invention, as nitrogenous nucleophilic compound, of compounds of the following types: ammonia, amines which may or may not be substituted by deprotectable groups, such as a benzyl group or one of its derivatives, amides, imides, sulphonamides, sulphonimides, hydrazines or azides.

According to a preferred alternative form of the claimed process, it is more preferably an organic organosoluble azide which can be generated in situ.

The leaving groups deriving from the activation of the hydroxyl functional group at the 4" position in the general formula II by a compound of formula IVA or IVB $$BSO_2X \text{ or} \quad\quad (IVA)$$
$$(BSO_2)_2O \quad\quad (IVB)$$

with:
- X being a halogen atom or a nitrogenous heterocycle, preferably an imidazole ring, and
- B being a $C_1$–$C_{20}$ alkyl, $C_5$–$C_6$ aryl or heteroaryl or $C_6$–$C_{26}$ alkylaryl group, which are or are not substituted by one or more halogen atoms, preferably fluorine, and/or a nitro, cyano or trifluoromethyl group, are very particularly suitable for the invention.

The compound of general formula III thus obtained is preferably brought into contact with an organosoluble azide in order to result, by stereoselective nucleophilic displacement, in a compound of general formula V

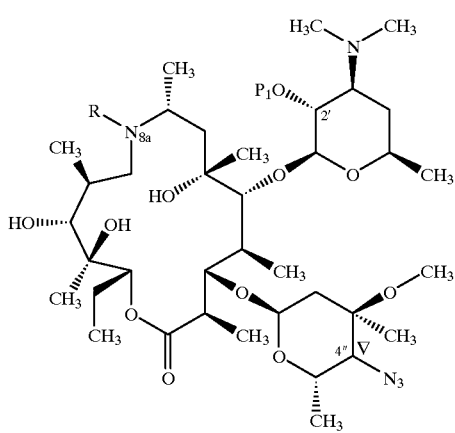

(V)

in which R and $P_1$ are as defined in general formula I and ∇ means that the C in the 4" position has undergone an inversion of configuration with respect to the formula II, The C-4" carbon of the compound II preferably has a S configuration and the C-4" carbon of the compound V a R configuration.

According to this alternative form of the claimed process, a reduction of the said compound of formula V can additionally be carried out, prior or otherwise to the deprotection of the hydroxyl functional group at the 2' position, so as to obtain a compound of general formula I in which A is a hydrogen atom. This reduction of the azide functional group can be carried out by any conventional method, such as those described by E. F. V. Scriven et al., Chem. Rev. (1988), 88, 297–368. A catalytic reduction with hydrogen or hydrazine in the presence of palladium-on-charcoal, for example, or of Raney nickel can in particular be carried out.

On conclusion of this reduction, the expected 4" (R)-$NH_2$ amino derivative, that is to say with inversion of configuration, is thus recovered with a satisfactory yield.

Consequently, this alternative form of the claimed process is very particularly of use in the preparation of the compounds of general formula I"

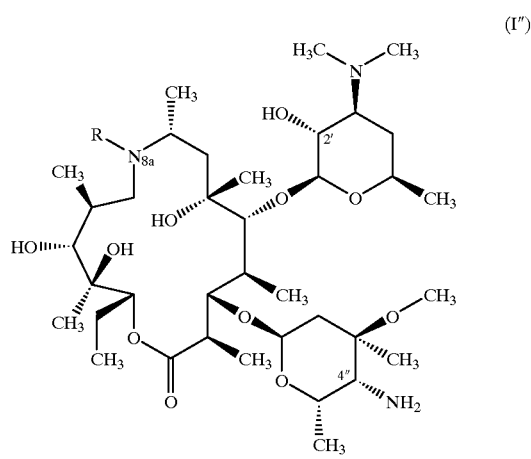

(I")

in which:
R is a hydrogen atom or a $C_1$–$C_{10}$ alkyl, $C_2$–$C_{10}$ alkenyl or $C_6$–$C_{12}$ arylsulphonyl group, which are, if appropriate, substituted, from a compound of general formula II as defined above.

Mention may very particularly be made, as illustration of the azides which are suitable for the present invention, of tetra($C_1$ to $C_{20}$ alkyl)ammonium or -phosphonium azide, substituted or unsubstituted triarylsulphoniums and hexa($C_1$ to $C_{20}$ alkyl)guanidiniums.

According to a preferred alternative form of the invention, it is a tetraalkylammonium azide and more particularly tetrabutyl- or tetraoctylammonium azide.

In a specific embodiment of the invention, the azide derivative is formed in a two-phase medium and more specifically in solid/liquid phase transfer. In this case, the organosoluble azide is generated in situ from an inorganic azide, such as sodium azide, and from a phase transfer agent in the presence of the compound of general formula III in an organic solvent. The phase transfer agent is preferably a tetra($C_1$ to $C_{20}$ alkyl)ammonium or -phosphonium methanesulphonate.

As regards the compound of general formula II, it is generally obtained beforehand by protection of the hydroxyl functional group at the 2' position in the corresponding derivative. Of course, this protection is carried out conventionally using a conventional protective group for the hydroxyl functional group, such as those which appear in "Protective Groups in Organic Synthesis", Second Edition, Theodora W. Greene and P. G. Wuts, Wiley Intersciences, p. 10–142. The procedures for carrying out the protecting and deprotecting operations are also described in the work referred to above.

Following this protection of the hydroxyl functional group at the 2' position, the hydroxyl functional group at the 4" position is activated. This activation of the compound of general formula II is also carried out under conventional operating conditions, such as those described in "Protective Groups in Organic Synthesis", Second Edition, Theodora W. Greene and P. G. M. Wuts, Wiley Intersciences, p. 117–118.

The examples submitted below describe a detailed procedure for the activation of the 4" hydroxyl functional group with triflic anhydride.

As regards the nucleophilic substitution reaction, it is carried out in an organic solvent, preferably an anhydrous organic solvent. In the preferred alternative form of the invention employing an organosoluble azide, aromatic solvents, such as benzene and toluene, or ethers, such as THF or methyl tert-butyl ether, are suitable in particular as solvents.

The nitrogenous nucleophilic compound, preferably the azide, is used in a proportion of approximately 1 to 30 equivalents with respect to the compound of formula III and preferably in a proportion of approximately 1 to 5 equivalents.

The temperature is conventionally between −20 and 180° C. As a general rule, it is adjusted so as to favour the kinetics of the reaction without harming the stability of the compounds.

According to a preferred alternative form of the invention, in the first stage, the hydroxyl functional group at the 4" position is activated by a trifluoromethanesulphonate group and the nucleophilic substitution is carried out with inversion of configuration with tetrabutyl- or tetraoctylammonium azide in toluene at room temperature.

According to a preferred alternative form of the invention, R is a methyl group in the general formulae I, I', II', II", III and V and A a hydrogen atom in the general formula I and I'.

Another subject-matter of the present invention is the compounds of general formula VI

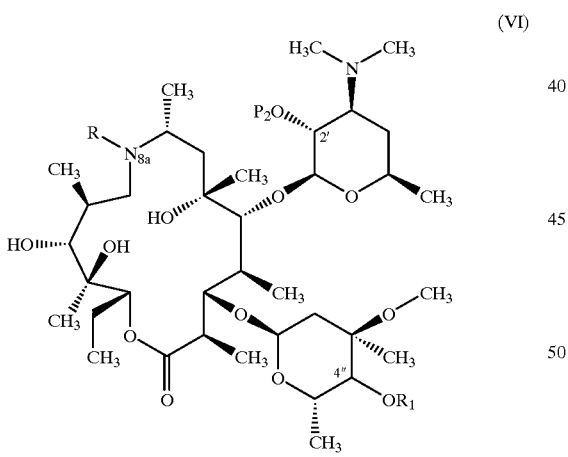

(VI)

in which

P$_2$ is a hydrogen atom or a protective group,

R is a hydrogen atom or a C$_1$–C$_{10}$ alkyl, C$_2$–C$_{10}$ alkenyl or C$_6$–C$_{12}$ arylsulphonyl group, which are, if appropriate, substituted, and OR$_1$ is a leaving group, as intermediates in the preparation of a compound of general formula I.

More preferably, R is a methyl group and OR$_1$ is a triflate group and more preferably the C-4" carbon has a R configuration.

The present invention also relates to the compounds of general formula VII

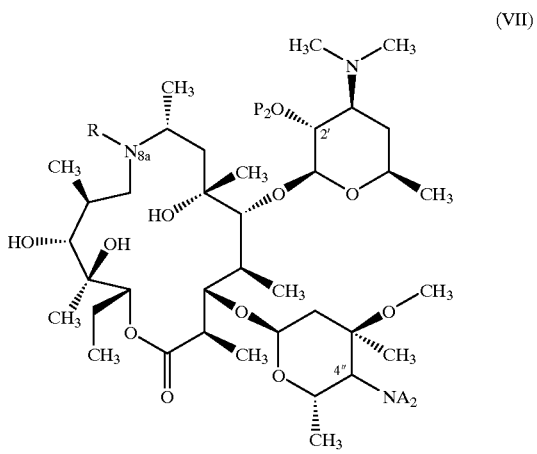

(VII)

in which

P$_2$ is a hydrogen atom or a protective group,

R is a hydrogen atom or a C$_1$–C$_{10}$ alkyl, C$_2$–C$_{10}$ alkenyl or C$_6$–C$_{12}$ arylsulphonyl group, which are, if appropriate, substituted, and A, which are identical or different, are a nitrogen atom, if appropriate substituted, a C$_1$–C$_4$ alkyl group, which is optionally substituted by one or more aryl groups, which are, if appropriate, substituted, as intermediates in the preparation of a compound of general formula I.

More preferably, R is a methyl group and NA$_2$ an N$_3$ group and more preferably, the C-4" carbon has a R configuration.

The examples which appear below are presented by way of illustration and without implied limitation of the present invention.

EXAMPLE 1

Preparation of the compound 4"-dehydroxy-4" (R)-amino-2'-acetoxy-9-deoxo-8a-aza-8a-methyl-8a-homoerythromycin A:

The synthetic scheme used is as follows:

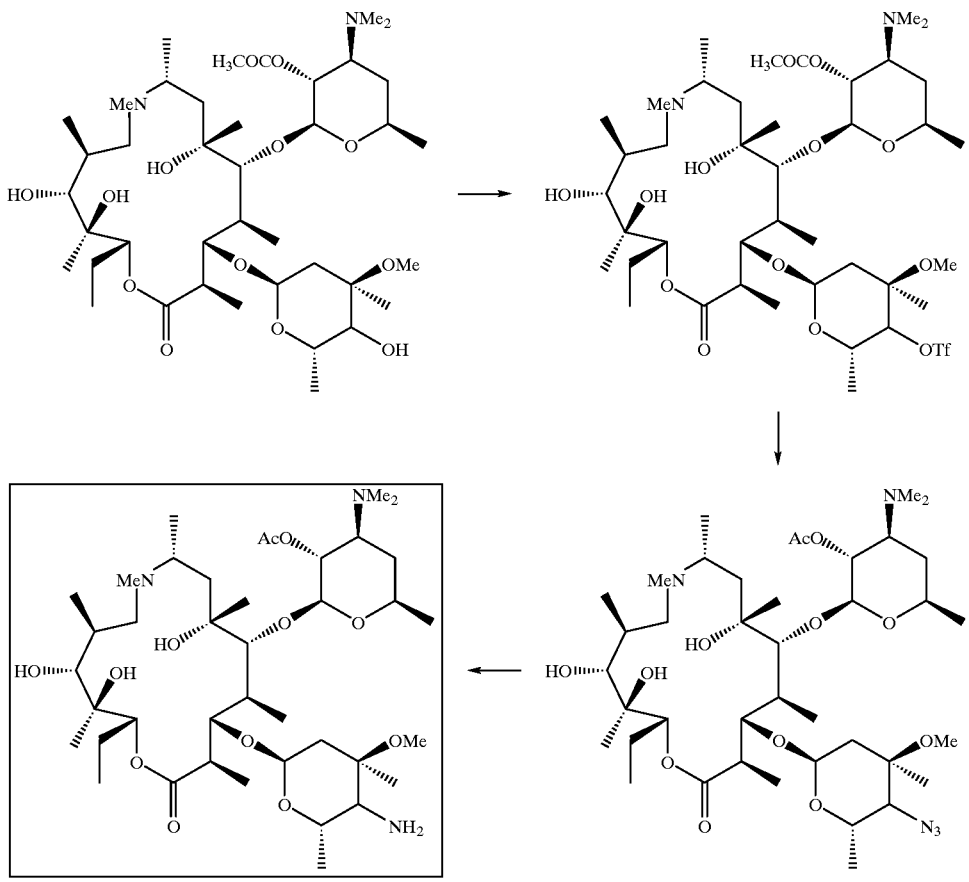

All the tests are carried out under an inert atmosphere.

1) Formation of 4" (S)-trifluoromethylsulphonyl-2'-acetoxy-9-deoxo-8a-aza-8a-methyl-8a-homoerythromycin A:

Pyridine (39.5 mg, 0.51 mmol, 5 equiv.) is added to a solution of alcohol 2'-acetoxy-9-deoxo-8a-aza-8a-methyl-8a-homoerythromycin A (0.1 g, 0.12 mmol, 1 equiv.) in anhydrous dichloromethane (0.4 ml). The solution is cooled to 0° C. and then a solution of triflic anhydride (42.3 mg, 0.15 mmol, 1.2 equiv.) is added dropwise. The solution is stirred for 1 h at 0° C. and then 30 min at room temperature. After diluting the reaction mixture with anhydrous dichloromethane (10 ml), the reaction mixture is cooled to 0° C. and then hydrolysed by addition of a saturated aqueous sodium bicarbonate solution (10 ml). The organic phase is separated and then washed with distilled water (10 ml), dried over magnesium sulphate and evaporated. The crude product is taken up in heptane (10 ml) in order to remove any trace of residual pyridine by azeotropic distillation. 110.4 mg of 4" (S)-trifluoromethylsulphonyl-2'-acetoxy-9-deoxo-8a-aza-8a-methyl-8a-homo-erythromycin A are obtained with a purity greater of than or equal to 90%. The structure is confirmed by NMR and MS analysis.

2) Formation of 4"-dehydroxy-4" (R)-azido-2'-acetoxy-9-deoxo-8a-aza-8a-methyl-8a-homoerythromycin A:

A 0.58M solution of tetrabutylammonium azide in toluene (4.5 ml; app. 1.3 equiv.) is added to unpurified 4" (S)-trifluoromethylsulphonyl-2'-acetoxy-9-deoxo-8a-aza-8a-methyl-8a-homoerythromycin A from the preceding stage (1.84 g, 2.0 mmol, 1 equiv.) at room temperature. The reaction mixture is stirred for 3 days at room temperature and then diluted with toluene (25 ml). This solution is washed three times with distilled water (3×10 ml), then dried over magnesium sulphate and evaporated. 1.63 g of 4"-dehydroxy-4"(R)-azido-2'-acetoxy-9-deoxo-8a-aza-8a-methyl-8a-homo-erythromycin A are obtained with a purity of 70%. The structure is confirmed by NMR and MS analysis.

3) Formation of the compound 4"-dehydroxy-4" (R)-amino-2'-acetoxy-9-deoxo-8a-aza-8a-methyl-8a-homoerythromycin A:

Raney nickel (200 mg) is added to a solution in isopropanol (5 ml) of unpurified 4"-dehydroxy-4"(R)-azido-2'-acetoxy-9-deoxo-8a-aza-8a-methyl-8a-homo-erythromycin A from the preceding stage (250.0 mg, 0.30 mmol, 1 equiv.). Hydrazine monohydrate (30 microliters, 0.6 mmol, 2 equiv.) is added every 30 minutes. The reaction time is 2 h. The reaction mixture is diluted with ethyl acetate (10 ml) and filtered. The filtrate is washed with a saturated aqueous sodium bicarbonate solution (10 ml) and then with water (10 ml). After drying over magnesium sulphate, the filtrate is evaporated. 230 mg of 4"-dehydroxy-4" (R)-amino-2'-acetoxy-9-deoxo-8a-aza-8a-methyl-8a-homoerythromycin A are obtained with a purity of 60%. The structure is confirmed by NMR and MS analysis.

EXAMPLE 2

Tetraoctylammonium azide (190.3 ml, 0.5 mmol, 5 equiv.) is added at room temperature to a solution of 4"

(S)-trifluoromethylsulphonyl-2'-acetoxy-9-deoxo-8a-aza-8a-methyl-8a-homoerythromycin A (92.3 mg, 0.1 mmol, 1 equiv.) in toluene (0.2 ml). After stirring for two days at room temperature, tetraoctylammonium azide (58 mg, 0.15 mmol, 1.5 equiv.) is again added. After stirring for an additional two days at room temperature, the reaction mixture is diluted with toluene (10 ml) and washed with water (10 ml). The organic phase is separated and dried over sodium sulphate. After evaporating the solvents, $^1$H NMR analysis shows the predominant presence of the compound 4"-dehydroxy-4" (R)-azido-2'-acetoxy-9-deoxo-8a-aza-8a-methyl-8a-homoerythromycin A.

EXAMPLE 3

Tetrabutylphosphonium methanesulphonate (355 mg, 1 mmol, 5 equiv.) and then sodium azide (325 mg, 5 mmol, 25 equiv.) are successively added to a solution of 4" (S)-trifluoromethylsulphonyl-2'-acetoxy-9-deoxo-8a-aza-8a-methyl-8a-homoerythromycin A (185 mg, 0.2 mmol, 1 equiv.) in toluene (0.4 ml) at room temperature. After stirring for three days at room temperature, the reaction mixture is diluted with toluene (10 ml) and washed with water (10 ml). The organic phase is separated and dried over sodium sulphate. After evaporating the solvents, $^1$H NMR analysis shows the predominant presence of the compound 4"-dehydroxy-4" (R)-azido-2'-acetoxy-9-deoxo-8a-aza-8a-methyl-8a-homoerythromycin A.

EXAMPLE 4

Tetraoctylammonium methanesulphonate (217 mg, 0.38 mmol, 3.8 equiv.) and then tetrabutylammonium azide (158 mg, 2.5 mmol, 25 equiv.) are successively added to a solution of 4" (S)-trifluoromethylsulphonyl-2'-acetoxy-9-deoxo-8a-aza-8a-methyl-8a-homoerythromycin A (92 mg, 0.1 mmol, 1 equiv.) in toluene (0.25 ml) at room temperature. After reacting for 4 days at room temperature, the reaction mixture is diluted with toluene (10 ml) and washed with water (10 ml). The organic phase is separated and dried over sodium sulphate. After evaporating the solvents, $^1$H NMR analysis shows the predominant presence of the compound 4"-dehydroxy-4" (R)-azido-2'-acetoxy-9-deoxo-8a-aza-8a-methyl-8a-homoerythromycin A.

EXAMPLE 5

A solution of 4" (S)-trifluoromethylsulphonyl-2'-acetoxy-9-deoxo-8a-aza-8a-methyl-8a-homoerythromycin A (21.4 mg, 0.023 mmol) in N-methylpyrrolidinone is saturated with gaseous ammonia. This solution is stirred for 48 h at room temperature. The reaction mixture is subsequently diluted with ethyl acetate (10 ml) and washed with water (15 ml). The organic, phase is separated, dried over sodium sulphate and evaporated. LC/MS analysis shows the formation of 22%, by internal standardization, of 4"-dehydroxy-4" (R)-amino -2'-acetoxy-9-deoxo-8a-aza-8a-methyl-8a-homoerythromycin A.

What is claimed is:

1. A process for the stereoselective preparation of a compound of formula I

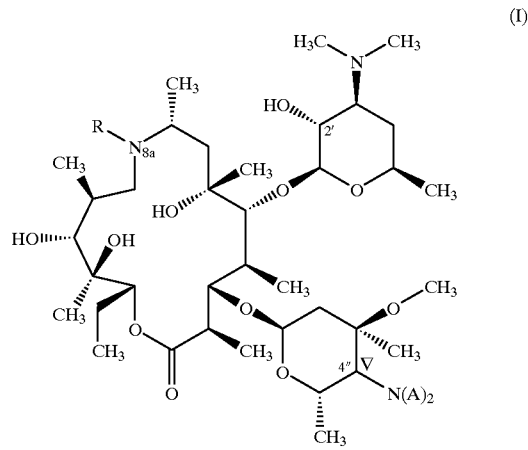

(I)

wherein:

R is a hydrogen atom or a $C_1$–$C_{10}$ alkyl, $C_2$–$C_{10}$ alkenyl or $C_6$–$C_{12}$ arylsulphonyl group, optionally substituted;

A, each of which is identical or different, is
  a hydrogen atom,
  a nitrogen atom, otionally substituted,
  a $C_1$–$C_4$ alkyl group, which is optionally substituted by one or more aryl groups, which are, in turn, optionally substituted,
  an $R_2CO$ or $R_2SO_2$ group, with $R_2$ being a hydrogen atom, a $C_1$–$C_8$ alkyl group or an aryl group, which are, optionally substituted; and ∇ indicates that the C in the 4" position has undergone an inversion of configuration with respect to the formula II, from a compound of formula II:

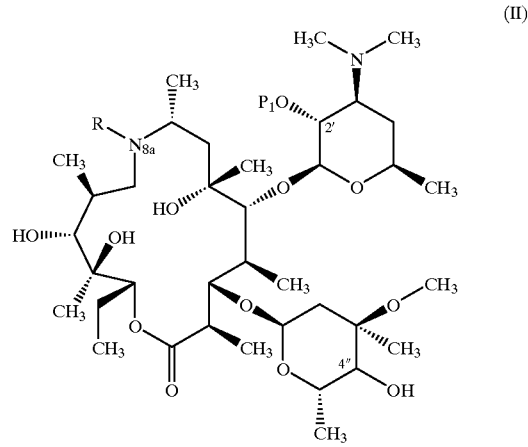

(II)

wherein:

R as defined in formula I and $P_1$ is a protective group for the hydroxyl functional group at the 2' position, comprising the steps of:

(i) activating the hydroxyl functional group at the 4" position in the compound of formula II, in order to obtain a compound of formula III:

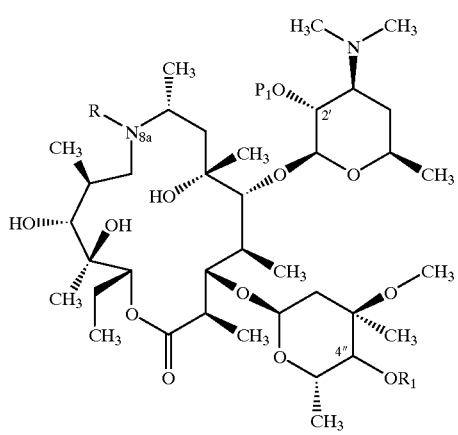

(III)

wherein:

R and $P_1$ are as defined in formulae I and II and $OR_1$ is a leaving group;

(ii) contacting the compound of formula III with a nitrogenous nucleophilic derivative under conditions which are sufficient to allow the stereoselective displacement of the hydroxyl functional group activated by the said nitrogenous nucleophile; and (iii) deprotecting the hydroxyl functional group at the 2' position.

2. The process according to claim 1, wherein a 4"-(R)—$NA_2$ of formula I':

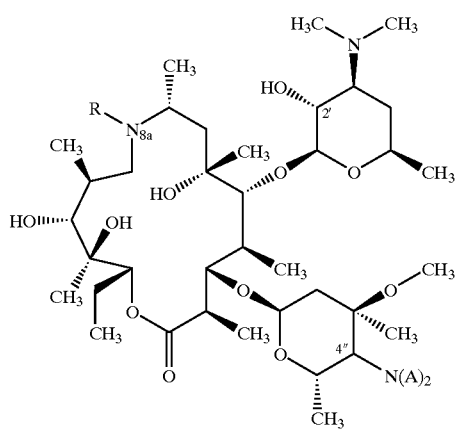

(I')

wherein A and R are as defined in claim 1, is prepared from a 4"-(S)—OH derivative of formula II':

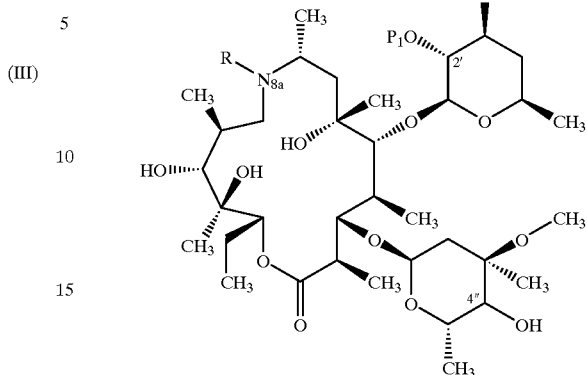

(II')

wherein R and $P_1$ are as defined in claim 1.

3. The process according to claim 1, wherein the leaving group represented by $OR_1$ in formula III is selected from the group consisting of $C_1$–$C_{20}$ alkyl sulphonates, $C_5$–$C_6$ aryl sulphonates, $C_5$–$C_6$ heteroaryl sulphonates and $C_6$–$C_{26}$ alkylaryl sulphonates, which are optionally substituted by one or more halogen atoms and/or a nitro, cyano or trifluoromethyl group.

4. The process according to claim 1, wherein the leaving group represented by $OR_1$ in formula III is a triflate group.

5. The process according to claim 1, wherein the leaving group derives from the activation of the hydroxyl functional group at the 4" position in the formula II by a compound of formula IVA or IVB:

$$BSO_2X \quad \text{or} \quad (BSO_2)_2O \qquad \text{IVA or IVB}$$

wherein:

X is a halogen atom or a nitrogenous heterocycle; and

B is a $C_1$–$C_{20}$ alkyl, $C_5$–$C_6$ aryl or heteroaryl, or $C_6$–$C_{26}$ alkylaryl group, which is optionally substituted by one or more halogen atoms and/or a nitro, cyano or trifluoromethyl group.

6. The process according to claim 1, wherein the nitrogenous nucleophilic compound is selected from the group consisting of ammonia and amines, optionally substituted by deprotectable groups, amides, imides, sulphonamides, sulphonimides, hydrazines or azides.

7. The process according to claim 1, wherein the nitrogenous nucleophilic compound is used in a proportion of approximately 1 to 30 equivalents with respect to the compound of formula III.

8. The process to claim 1, wherein the nitrogenous nucleophilic compound is an organic organosoluble azide, optionally generated in situ.

9. The process according to claim 1, further comprising:

activating the compound of formula II with a compound of formula IVA or IVB $$BSO_2X \quad \text{or} \qquad \text{IVA}$$
$$(BSO_2)_2O \qquad \text{IVB}$$

wherein:

X is a halogen atom or a nitrogenous heterocycle; and

B is a $C_1$–$C_{20}$ alkyl, $C_5$–$C_6$ aryl or heteroaryl or $C_6$–$C_{26}$ alkylaryl group, which are optionally substituted by one or more halogen atoms and/or a nitro, cyano or trifluoromethyl group; and contacting the compound of formula III with an organic organosoluble azide in order to result, by stereoselective nucleophilic displacement, in a compound of formula V

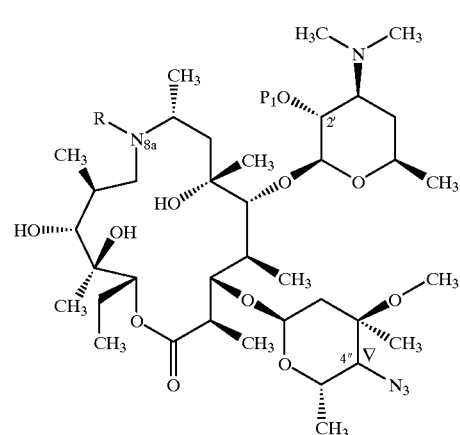

(V)

wherein R and $P_1$ are as defined in formula I and $\nabla$ indicates that the C in the 4" position has undergone an inversion of configuration with respect to the formula II.

10. The process according to claim 1, further comprising:

activating the compound of formula II with a compound of formula IVA or IVB $$BSO_2X \quad \text{or} \qquad \text{IVA}$$

$$(BSO_2)_2O \qquad \text{IVB}$$

wherein:

X is a halogen atom or a nitrogenous heterocycle, and

B is a $C_1$–$C_{20}$ alkyl, $C_5$–$C_6$ aryl or heteroaryl or $C_6$–$C_{26}$ alkylaryl group, optionally substituted by one or more halogen atoms and/or a nitro, cyano or trifluoromethyl group;

contacting the compound of formula III with an organic organosoluble azide resulting, by stereoselective nucleophilic displacement, in a compound of formula V:

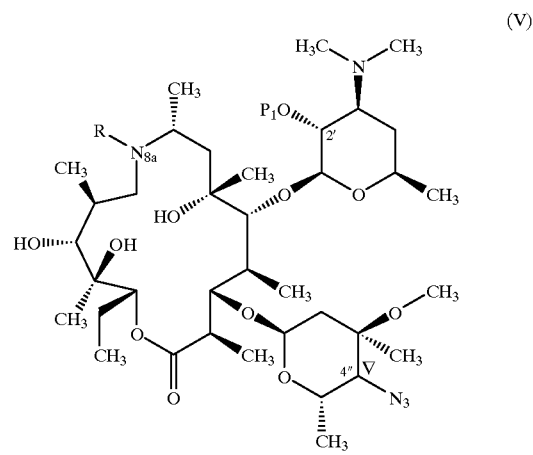

(V)

wherein:
R and $P_1$ are as defined in formula I and $\nabla$ means that the C in the 4" position has undergone an inversion of configuration with respect to the formula II; and reducing the compound of formula V, so as to obtain a compound of formula I in which A is a hydrogen atom.

11. The process according to claim 1, further comprising:

activating the compound of formula II with the C-4" carbon having S configuration with a compound of formula IVA or IVB $$BSO_2X \quad \text{or} \qquad \text{IVA}$$

$$(BSO_2)_2O \qquad \text{IVB}$$

wherein:

X is a halogen atom or a nitrogenous heterocycle, and

B is a $C_1$–$C_{20}$ alkyl, $C_5$–$C_6$ aryl or heteroaryl or $C_6$–$C_{26}$ alkylaryl group, optionally substituted by one or more halogen atoms and/or a nitro, cyano or trifluoromethyl group;

contacting the compound of formula III with an organic organosoluble azide in order to result, by stereoselective nucleophilic displacement, in a compound of formula V

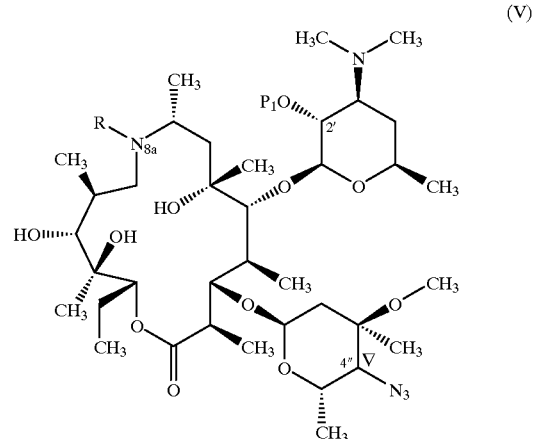

(V)

wherein R and P₁ are as defined in formula I, the C-4" carbon has a R configuration and ∇ indicates that the C in the 4" position has undergone an inversion of configuration with respect to the formula II.

12. The process according to claim 1, wherein the nitrogenous nucleophilic compound is an organic organosoluble azide selected from the group consisting of tetra-($C_1$ to $C_{20}$ alkyl) ammonium azide, tetra-($C_1$ to $C_{20}$ alkyl) phosphonium azide, substituted or unsubstituted triarylsulphoniums and hexa ($C_1$ to $C_{20}$ alkyl)-guanidiniums.

13. The process according to claim 1, wherein the nitrogenous nucleophilic compound is a tetrabutylammonium azide or tetraoctylammonium azide.

14. The process according to claim 1, wherein the nitrogenous nucleophilic compound is an organic organosoluble azide and the nucleophilic displacement of the leaving group at the 4" position by the organic organosoluble azide is carried out in a solvent selected from the group consisting of aromatic solvents and ethers.

15. The process according to claim 1, wherein, in the first stage, the hydroxyl functional group at the 4" position is activated by a trifluoromethanesulphonate group and the nucleophilic substitution is carried out with inversion of configuration with tetrabutyl-ortetraoctylammonium azide in toluene at room temperature.

16. The process according to claim 1, wherein R is a methyl group in the formulae I, I', I", II, II', III and V and A a hydrogen atom in the formula I and I'.

17. A compound of formula VI

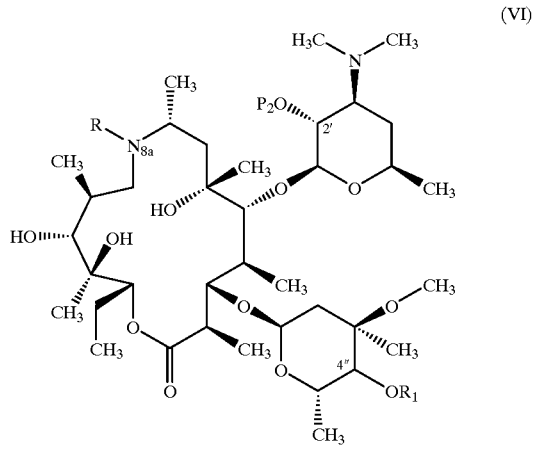

(VI)

wherein:

P₂ is a hydrogen atom or a protective group;

R is a hydrogen atom or a $C_1$–$C_{10}$ alkyl, $C_2$–$C_{10}$ alkenyl or $C_6$–$C_{12}$ arylsulphonyl group, optionally substituted; and OR₁ is a leaving group.

18. The compound of formula VI according to claim 17, wherein R is a methyl group and OR₁ is a triflate group.

19. The compound of formula VI according to claim 18, wherein the C-4" carbon has a S configuration.

20. A compound of formula VII

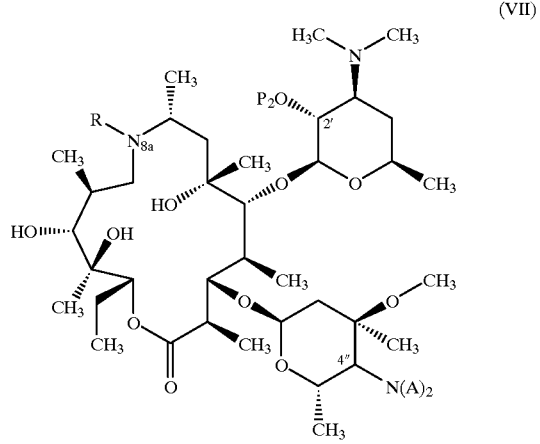

(VII)

wherein:

P₂ is a hydrogen atom or a protective group;

R is a hydrogen atom or a $C_1$–$C_{10}$ alkyl, $C_2$–$C_{10}$ alkenyl or $C_6$–$C_{12}$ arylsulphonyl group, optionally substituted; and A, each of which is identical or different, is
  a nitrogen atom, optionally substituted, or
  a $C_1$–$C_4$ alkyl group, which is optionally substituted by one or more aryl groups, which are, in turn, optionally substituted, wherein A is not a hydrogen atom or a R₂CO or R₂SO₂ group, with R₂ being a hydrogen atom, a $C_1$–$C_8$ alkyl group or an aryl group, which are, optionally substituted.

21. The compound of formula VII according to claim 20, wherein R is a methyl group and N(A)₂ is a N₃ group.

22. The compound of formula VI according to claim 20, wherein the C-4" carbon has a R configuration.

23. The process according to claim 3, wherein the halogen atom is fluorine.

24. The process according to claim 5, wherein the nitrogenous heterocycle is an imidazole ring.

25. The process according to claim 5, wherein the halogen atom is fluorine.

26. The process according to claim 9, wherein the nitrogenous heterocycle is an imidazole.

27. The process according to claim 10, wherein the nitrogenous heterocycle is an imidazole.

28. The process according to claim 10, wherein the halogen atom is fluorine.

29. The process according to claim 11, wherein the nitrogenous heterocycle is an imidazole.

30. The process according to claim 11, wherein the halogen atom is fluorine.

31. The process according to claim 14, wherein the ether is selected from the group consisting of methyl tert-butyl ether and THF.

32. The process according to claim 14, wherein the solvent is selected from the group consisting of benzene and toluene.

* * * * *

UNITED STATES PATENT AND TRADEMARK OFFICE
CERTIFICATE OF CORRECTION

PATENT NO.   : 6,353,096 B1                                                Page 1 of 1
DATED        : March 5, 2002
INVENTOR(S)  : Patrick Leon It is certified that error appears in the above-identified patent and that said Letters Patent is hereby corrected as shown below:

<u>Column 12,</u>
Line 31, change "otionally" to -- optionally --.

Signed and Sealed this

Fourth Day of June, 2002

Attest:

Attesting Officer

JAMES E. ROGAN
Director of the United States Patent and Trademark Office